United States Patent [19]

Akabane et al.

[11] Patent Number: 4,645,569
[45] Date of Patent: Feb. 24, 1987

[54] PROCESS FOR PRODUCING ANHYDROUS ETHANOL

[75] Inventors: Toshiaki Akabane, Yukigayaohtsukamachi; Arimasa Satoh, Funabashishi, both of Japan

[73] Assignee: Shinnenryoyu Kaihatsugijutsu Kenkyukumiai, Tokyo, Japan

[21] Appl. No.: 554,314

[22] Filed: Nov. 22, 1983

[30] Foreign Application Priority Data

Nov. 29, 1982 [JP] Japan .................. 57-208984

[51] Int. Cl.$^4$ .............. B01D 3/36; B01D 1/28; C07C 29/82
[52] U.S. Cl. ..................... 203/19; 203/25; 203/26; 203/81; 203/100; 203/DIG. 4; 203/DIG. 8; 203/DIG. 13; 203/DIG. 16; 62/476; 202/154; 568/916
[58] Field of Search ............ 203/19, 26, DIG. 4, 203/DIG. 20, DIG. 13, 74, 81, 25, 100, DIG. 16, 24, DIG. 8; 62/476; 202/154; 435/161; 568/916; 426/494

[56] References Cited

U.S. PATENT DOCUMENTS

| | | | |
|---|---|---|---|
| 1,860,554 | 5/1932 | Ricard et al. | 203/19 |
| 2,509,136 | 5/1950 | Cornell | 203/21 |
| 4,209,364 | 6/1980 | Rothschild | 203/11 |
| 4,217,178 | 8/1980 | Katzen et al. | 203/DIG. 13 X |
| 4,306,940 | 12/1981 | Zenty | 203/DIG. 13 X |
| 4,308,106 | 12/1981 | Mannfeld | 203/DIG. 13 X |
| 4,309,254 | 1/1982 | Dahlstrom et al. | 203/19 X |
| 4,329,206 | 5/1982 | Cartland | 203/19 X |
| 4,340,446 | 7/1982 | Crawford | 203/26 X |
| 4,402,795 | 9/1983 | Erickson | 203/19 X |

Primary Examiner—Wilbur Bascomb
Attorney, Agent, or Firm—Fred Philpitt

[57] ABSTRACT

A process for producing anhydrous ethanol, using an apparatus comprising a combination of a concentration column, an azeotropic distillation column and a solvent recovery column, and capable of effectively utilizing the vapor at the tops of the concentration column and the azeotropic distillation column, is provided, which process comprises:
(i) connecting an absorption type heat pump functioning as a condenser and a reboiler at the same time, to either one of the concentration column or the azeotropic distillation column;
(ii) connecting a combination of a mechanical type heat pump with a heat exchanger functioning as a condenser and a reboiler at the same time to another of the columns;
(iii) using a back pressure turbine as a machine for driving the mechanical type heat pump; and
(iv) using the back pressure steam generated by operating the mechanical type heat pump as the heat source for the absorption type heat pump.

1 Claim, 2 Drawing Figures

PROCESS FOR PRODUCING ANHYDROUS ETHANOL

BACKGROUND OF THE INVENTION

1. Field of the Invention

This invention relates to a process and an apparatus for producing anhydrous ethanol. More particularly it relates to a process and an apparatus wherein an absorption heat pump and a mechanical heat pump are included in a process and an apparatus for producing anhydrous ethanol from dilute ethanol using a concentration column, an azeotropic distillation column and a solvent recovery column.

2. Description of the Prior Art

As for processes and apparatus for obtaining anhydrous ethanol from dilute ethanol by concentration through distillation, those consisting of a combination of a concentration column, an azeotropic distillation column and a solvent recovery column have generally been conventionally employed, and steam has often been used as the heat source therefor. In order to save the steam, i.e. as an energy saving feature, if the steam at the top of the distillation column is compressed and pressure-elevated by means of a compressor, the steam temperature at the top is considerably higher than the temperature in the case of condensation at atmospheric pressure. A process of heating the boiler liquid of the column by the compressed steam has been known.

However, when an electric motor is used as the machine for driving such a compressor, a considerably high amount of electric power is consumed for driving the compressor. Thus, the use of such a compressor is impractical in districts where electric power is not available or in districts where electric power is supplied at a high cost.

On the other hand, in such districts, if dilute ethanol which has been obtained from agricultural materials according to a fermentation process is used as the raw material, a large amount of steam is obtained by operating a boiler using as fuel therefor residue from the agricultural products such as bagasse.

When utilizing such steam as the power source of the compressor, it may be considered to employ a steam turbine as the machine for driving the compressor. However, in the case where the turbine is a condensation turbine, a large part of the heat quantity of steam used is transferred to cooling water in the condenser; hence such a process is uneconomical.

The present inventors have made strenuous studies on effective utilization of waste heat in the case where a steam turbine is employed, and as a result, have found that the waste heat can be utilized as the heat source for an absorption heat pump and as the heat source for the reboiler of a solvent recovery column. With respect to the absorption heat pump, if the heat quantity of the vapor at the top of a concentration column or an azeotropic distillation column is utilized for heating the boiler liquid of the respective columns, then the heat source for the absorption heat pump itself is not required; hence the heat quantity of the steam used for the steam turbine can be effectively utilized to a large extent in accordance with the present invention.

As is apparent from the foregoing, an object of the present invention is to provide a process and an apparatus for employing a heat pump in order to effectively utilize the heat quantity of steam at the top of an apparatus for producing anhydrous alcohol, and to provide a process and apparatus for producing anhydrous alcohol wherein a steam turbine is employed whereby the heat quantity of the steam used for the turbine can be effectively utilized. Other objects will be apparent from the following description.

SUMMARY OF THE INVENTION

The present invention has the following two main aspects:

(1) In a process for producing anhydrous ethanol from dilute ethanol as a raw material by the use of an apparatus comprising a combination of a concentration column, an azeotropic distillation column and a solvent recovery column in this order, the improvement which comprises:

(i) connecting an absorption heat pump which functions as a condenser and a reboiler at the same time, to either the concentration column or the azeotropic distillation column;

(ii) connecting a combination of a mechanical heat pump with a heat exchanger functioning as a condenser and a reboiler at the same time to another of said columns;

(iii) using a back pressure turbine as a machine for driving the mechanical heat pump; and (iv) using the back pressure steam exhausted from the mechanical heat pump as the heat source for the absorption heat pump.

(2) An apparatus for producing anhydrous ethanol which comprises a combination of a concentration column, an azeotropic distillation column and a solvent recovery column in this order and wherein (i) an absorption heat pump L functioning as a condenser and a reboiler at the same time is connected to either the concentration column or the azeotropic distillation column; (ii) a combination of a mechanical heat pump D-F with a heat exchanger E functioning as a condenser and a reboiler at the same time is connected to another of said columns, and the back pressure turbine F of the mechanical heat pump is used as a machine for driving the mechanical heat pump; and (iii) the back pressure turbine F is connected to the heat pump L by a piping 10.

DETAILED DESCRIPTION OF THE INVENTION

The constitution and effectiveness of the present invention will be described in detail, referring to a concrete example shown in FIG. 1 and FIG. 2. Connection manner of A, B, C, D-F and L in FIG. 1 and FIG. 2 is described above, but in the present invention, a reverse connection manner thereto i.e. connection of D-F to A and L to B may also be employed.

Figure 1:
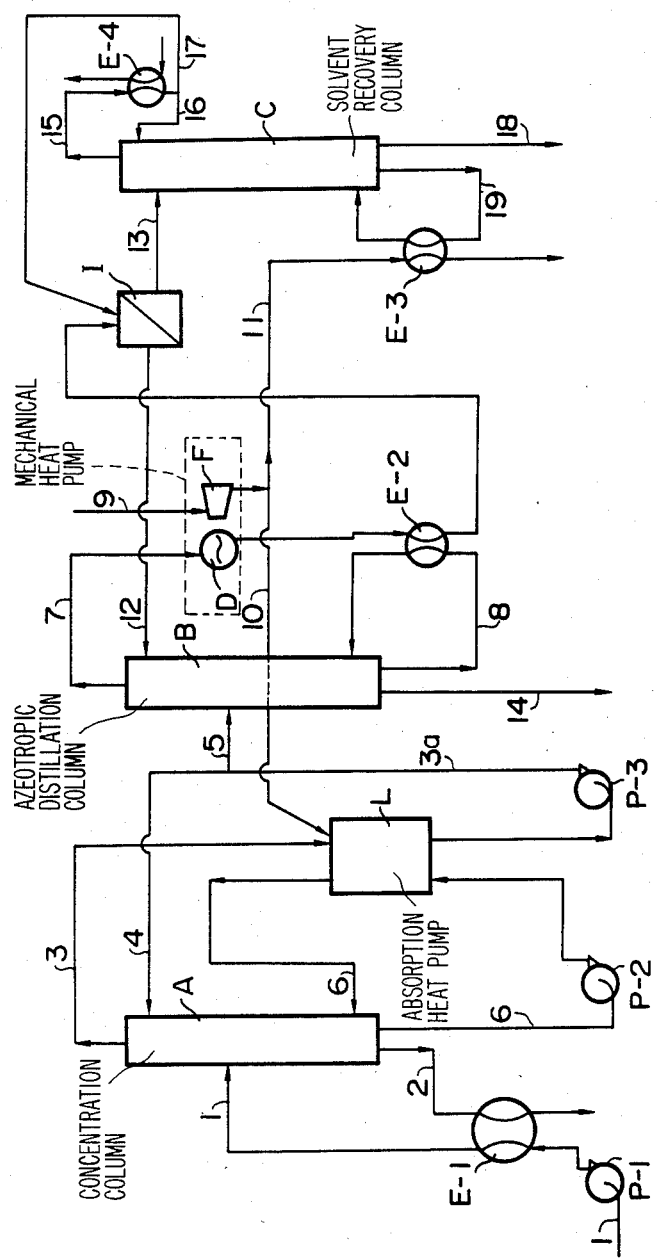
FIG. 1 shows a flow sheet of the apparatus for producing anhydrous ethanol of the present invention wherein a concentration column A, an azeotropic distillation column B and a solvent recovery column C are combined, and an absorption heat pump L is connected to the concentration column and a mechanical (compression type) heat pump D-F is connected to the azeotropic distillation column.

In FIG. 1, a dilute ethanol raw material such as "moromi" (a Japanese term; a mash) prepared according to a fermentation process (ethanol content: 1–6% by mol) is fed to a middle stage of the concentration column A through a pump P-1 and a piping 1. During the feed, the raw material is preheated in a heat exchanger E-1 by the waste water from the boiler of the column A. The raw material is concentrated by distillation in the column A, and ethanol-water vapor from the top of the column enters the absorption type heat pump L through a piping 3, while a portion of the boiler liquid is discharged from the bottom of the column via a piping 2 as waste water.

Figure 2:
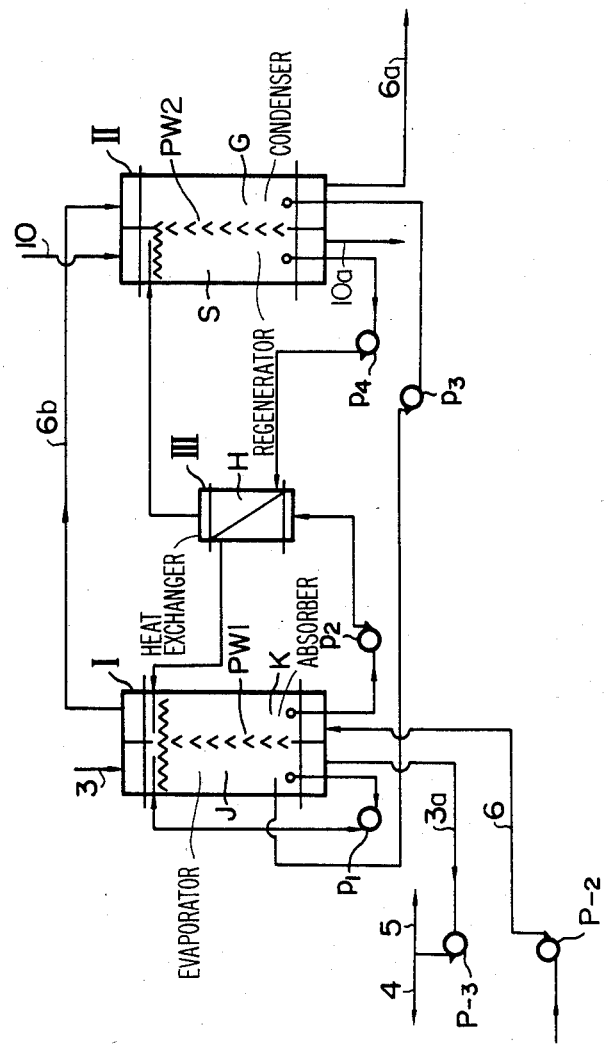
FIG. 2 shows the details of the absorption type heat pump L wherein J is an evaporator, K is an absorber, S is a regenerator, G is a condenser, and H is a heat exchanger.

Now, the present invention will be described referring to FIG. 2 illustrating the details of the absorption heat pump L.

The pump L comprises a member I composed integrally of an evaporator J and an absorber K, a member II composed integrally of a regenerator S and a condenser G and a member III consisting of a heat exchanger H. These members each are connected therebetween or to the respective columns, etc. as shown in FIG. 1, through pipings necessary therefor, and necessary pumps P-1-P-4) are interposed at the respective suitable locations of the pipings. These members each consist of a shell and tube heat exchanger. Concretely, the above-mentioned vapor from the top of the column A is introduced into the absorption heat pump L through the piping 3, is led into the tubes of the evaporator J in FIG. 2, and heats a cooling medium which flows down along the outer surface of the tubes in the form of liquid film to thereby vaporize a portion of the medium. The vapor itself condenses and then leaves the heat pump L. A portion of the condensate is returned to the column A as a reflux liquid via pipings 3a and 4 in FIG. 1, while another portion is fed to a middle stage of the azeotropic distillation column B through pipings 3a and 5 of FIG. 1.

Again referring to FIG. 2, the boiler liquid of the column A is introduced through a piping 6 and the pump P-2 in FIG. 1 into the tubes of the absorber K which is constructed so that the absorber K and the evaporator J can embrace one another as partners constituting the member I.

Now, the principle of the absorption heat pump consists in utilizing the fact that the equilibrium temperature of the absorbing solution is higher than the saturation temperature of the cooling medium. In the present invention, a case where water is used as the cooling medium and a LiBr-H$_2$O solution is used as the absorbing solution will be illustrated.

If the concentration column A in FIG. 1 is operated under atmospheric pressure and the dilute ethanol raw material feed is concentrated up to its azeotropic composition (note: ethanol, 85.94% by mol), then the vapor temperature at the top of the column is 78° C. and the temperature of the boiler liquid of the column (water) is 100° C., in view of the water-ethanol equilibrium relationship.

If the boiler part of the evaporator J is operated at 240 mmHg, then the cooling medium (water) vaporizes at 70° C. The evaporator J and the absorber K embrace one another as described above and there is provided therebetween a partition wall PW$_1$ through which the vapors of the vapor phases at the respective boiler parts of the vaporizer J and the absorber K can freely pass. The above-mentioned vapor of the cooling medium is introduced via this partition wall PW$_1$ from the vaporizer J into the absorber K, and absorbed in the absorbing solution (LiBr-H$_2$O) which is flowing down along the outer walls of the tubes in the form of thin film. If the initial concentration of the absorbing solution is 60% LiBr by weight and the concentration of the solution diluted by absorbing the vapor of the cooling medium is 55% LiBr by weight, then according to During Diagram of LiBr-H$_2$O (Handbook of Refrigeration Air Conditioning edited by Japan Refrigeration Association (Basic Edition), page 157, issued by Japan Refrigeration Association, July 20, 1976), it is seen that the absorption temperature is 110° C. Namely, the vapor generated at 70° C. is absorbed in the absorbing solution at a higher temperature of 110° C., releases its latent heat at this temperature and heats the boiler liquid (at 100° C.) of the concentration column A passing through the inside of the tubes in the absorber K.

The concentration of the LiBr-H$_2$O absorbing solution is reduced from 60% by weight down to 55% by weight, by absorbing the vapor of the cooling medium, and the dilute solution is sent to the boiler part of the regenerator S inside the member II via the inside of the tubes in the heat exchanger H. The dilute solution flows down along the outer surface of the tubes in the vessels in the form of a thin film. The regenerator S is a vessel for concentration by vaporization. The heat source for heating the vessel is the back pressure vapor from the machine F used for driving the mechanical heat pump (D-F in FIG. 1) as mentioned below. This back pressure vapor (at 179° C. where the pressure is 10 Kg/cm$^2$ obs.) is led into the tubes inside the regenerator S via a piping 10, heats the absorbing solution, and generates the vapor of the cooling medium which was previously absorbed in the LiBr solution thereby concentrating the absorbing solution up to the original concentration (60% LiBr by weight). The back pressure vapor thus used is discharged out through a piping 10a. The concentrated absorbing solution is returned again to the absorber K via the boiler part of the heat exchanger H. The regenerator S and the condenser G as partners constituting the member II in the absorption heat pump L are constructed so that they can embrace one another, and there can be provided therebetween a partition wall PW$_2$ through which the vapors of the vapor phases at the respective boiler parts of the regenerator S and the condenser G can freely pass. The above-mentioned vapor (steam) of the cooling medium generated in the regenerator S is led via the partition wall PW$_2$ from the regenerator S into the condenser G. On the other hand, the boiler liquid (at 100° C.) from the column A which is heated in the absorber K is led into the tubes in the condenser G via piping 6b. In this condenser G, the above-mentioned vapor of the cooling medium imparts its condensation latent heat to the boiler liquid from column A which is inside the tubes, and the cooling vapor itself condenses into water as a cooling medium, which is then sent to the evaporator J via pump P3.

If the regenerator S and the condenser G are operated under a pressure of 1300 mmHg inside their boiler parts, the condensation temperature of the vapor of the cooling medium will be 114° C., and this temperature will be sufficient for vaporizing the cooling medium by the back pressure vapor inside the regenerator S and for cooling and condensing the vapor by the boiler liquid A inside the condenser G. Viewing the path of the boiler liquid A, the liquid is heated in the absorber K and in the condenser G inside the absorption heat pump L and is returned to the bottom part of the column A. Since the composition of the liquid consists substantially of water, even when the pressure drop and the temperature difference between the upper and the lower parts of the column are taken into account, the temperature of the liquid is sufficient for vaporizing the boiler liquid in the column. In addition, in the heat-exchanger H in FIG. 2, heat-exchange is carried out between the dilute absorbing solution at a relatively low temperature leaving the absorber K and the concentrated absorbing solution at a relatively high temperature leaving the regenerator S.

As described above, the absorption heat pump of FIG. 2 makes it possible to utilize the vapor from the top of the column A which has a lower temperature as the heat source for the boiler liquid having a higher temperature, by employing a cooling medium and an absorbing solution and by utilizing the fact that the equilibrium temperature of the absorbing solution is higher than the saturation temperature of the vapor of the cooling medium. Now if the available efficiency of the heat quantity of the vapor is defined in terms of a ratio of the heat quantity which the absorption heat pump L receives from the vapor at the top of the column to the heat quantity which the cooling medium receives from the back pressure vapor in the regenerator S, as expressed by the following equation:

$$\eta = \frac{\left(\begin{array}{c}\text{Heat quantity released}\\ \text{in absorber } K\end{array}\right) + \left(\begin{array}{c}\text{Heat quantity released}\\ \text{in condenser } G\end{array}\right)}{\text{Heat quantity received in regenerator } S},$$

then $\eta = 1.7$ in the above case. If $\eta = 1.0$, there will be obtained only the same effectiveness as in the case where the boiler liquid is heated directly by the back pressure vapor.

Again referring to FIG. 1, the step where the azeotropic distillation column B is employed and the succeeding steps will be described. In FIG. 1, the distillate from the column A (i.e. condensate of the vapor at the top of the column) is sent to the azeotropic distillation column B via pipings 3a and 5. The column B is operated under atmospheric pressure, and the vapor is fractionated in the column B, to discharge a vapor comprising a ternary component system azeotrope of water-ethanol-solvent from the top of the column, while discharging a product (anhydrous ethanol) from the bottom of the column. The vapor of the azeotrope is sent via a piping 7 to the compressor D of the mechanical heat pump D-F where it is compressed to a pressure of 3 to 4 Kg/cm²G and an elevated temperature. The compressed vapor is then sent to the reboiler E-2 of the column, wherein it heats the boiler liquid of the column B which is circulated via a piping 8 to vaporize the boiler liquid at the bottom part of the column. The compressed vapor itself condenses and is sent to a decanter I (note: a pressure reducing valve provided between E-2 and I is not shown).

The compressor D-F employed in the present invention consists of the body D of the compressor and a machine F for driving the body D. A back pressure turbine is employed as the latter. Live steam is fed to the driving machine F through a piping 9, and a portion of the back pressure steam which is exhausted is sent via a piping 10 to the above-mentioned regenerator S (see FIG. 2) in the absorption heat pump L where it is utilized as a heat source. Another portion of the back pressure steam is sent via a piping 11 to the reboiler E-3 of the solvent recovery column C where it is utilized as a heat source for the boiler liquid of the column (waste water).

The above-mentioned distillate (the three-component azeotrope) from the column B is sent to the decanter I and is separated therein into an entrainer-rich phase and a water-rich phase, the former being returned to the vicinity of the top of the column B via piping 12 as a reflux liquid and the latter being fed via a piping 13 to the solvent-recovery column C. The water-rich phase which is fed to the column C is distilled and a water-ethanol-entrainer three-component vapor leaves the column at its top. This vapor is cooled and condensed in the condenser E-4 via a piping 15, a portion thereof being returned to the column C as a reflux liquid via a piping 16 and another portion, to the decanter I via a piping 17. A portion of the boiler liquid of the column C (water) is discharged from the bottom of the column as waste water via a piping 18. The heat necessary for the distillation in the column C is derived from the back pressure vapor of the machine F used for driving the steam turbine feed via piping 11 to the reboiler E-3 of the column. The boiler liquid of the column C is circulated to the reboiler E-3 via a piping 19.

As described above, according to the present invention, a mechanical heat pump is combined with either one of the concentration column or the azeotropic distillation column employed in the production of anhydrous ethanol from dilute ethanol; an absorption heat pump is combined with another of the columns; and a back pressure turbine is employed as the machine for driving the compressor of the former. Further, the back pressure obtained from the back pressure turbine is used not merely as the heat souce for the distillation in other columns, but as the heat source for concentrating the diluted heating medium in the above-mentioned absorption heat pump, whereby it is possible to promote power saving in both the heat pumps. Thus, the present invention is very advantageously employable in locations where the cost of electric power is high or it is difficult to avail a large quantity of electric power, and on the other hand, a fuel for low pressure boilers (such as agricultural wastes) is available.

What we claim is:

1. A method for producing anhydrous ethanol by the distillation of ethanol from water, comprising the steps of:

(a) concentrating an ethanol-water mixture to form an ethanol-water vapor by passing the mixture through a concentration distillation column including a bottoms liquid, the bottoms liquid of the concentration column being heated by an absorption heat pump and the ethanol-water vapor product from the concentration column being condensed in an evaporator provided in the absorption heat pump, a portion of the condensate being recycled to the concentration column and the remaining portion of the condensate being fed to an azeotropic distillation column;

(b) azeotropically distilling said remaining portion of condensed water-ethanol product from the concentration column in an azeotropic distillation column including a bottoms liquid by adding an entrainer liquid to the azeotropic distillation column to form an azeotropic ternary vapor product of water, ethanol and entrainer;

(c) compressing the azeotropic ternary vapor product using a mechanical heat pump including a compressor driven by a back pressure steam turbine to raise the pressure and temperature of the azeotropic ternary vapor product;

(d) passing the compressed azeotropic ternary product in heat exchange relation with the bottoms liquid of the azeotropic distillation column to heat the bottoms liquid and condense the azeotropic ternary product;

(e) supplying a portion of the back pressure steam exhausted from the mechanical heat pump to a regenerator provided in the absorption heat pump to provide the sole heat source for the absorption heat pump, the heat source serving to concentrate an absorbing solution previously diluted by absorption of a cooling medium vapor, both the absorbing solution and the cooling medium being circulated internally in the absorption heat pump and (f) recovering the entrainer from the azeotropic ternary product in a solvent recovery distillation column including a bottoms liquid, the bottoms liquid of the solvent recovery column being passed in heat exchange relation with another portion of the back pressure steam exhausted from the mechanical heat pump to effect the heating of the bottoms liquid, (g) utilizing live steam fed to a motor included in the mechanical heat pump as the sole heat source throughout all of the steps (a)–(f), and (h) recovering anhydrous ethanol from the azeotropic distillation column.

* * * * *